United States Patent
Wiegel

(10) Patent No.: US 8,287,488 B2
(45) Date of Patent: Oct. 16, 2012

(54) HOLOGRAPHIC OCCLUSION DETECTION SYSTEM FOR INFUSION PUMPS

(75) Inventor: Christopher Wiegel, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 300 days.

(21) Appl. No.: 12/633,283

(22) Filed: Dec. 8, 2009

(65) Prior Publication Data

US 2011/0137240 A1    Jun. 9, 2011

(51) Int. Cl.
*A61N 1/08* (2006.01)
(52) U.S. Cl. .................. 604/67; 604/93.01; 604/151
(58) Field of Classification Search ............ 604/67, 604/93.01, 151; 250/226; 73/705
See application file for complete search history.

(56) References Cited

U.S. PATENT DOCUMENTS

| | | | |
|---|---|---|---|
| 3,590,640 A | 7/1971 | Cindrich | |
| 4,355,898 A | 10/1982 | Dakin | |
| 4,620,093 A * | 10/1986 | Barkhoudarian et al. | 250/231.19 |
| 4,762,518 A | 8/1988 | Kreinick | |
| 4,939,368 A | 7/1990 | Brown | |
| 5,721,612 A | 2/1998 | Anderson | |
| 6,110,153 A | 8/2000 | Davis et al. | |
| 6,327,030 B1 | 12/2001 | Ifju et al. | |
| 6,587,211 B1 | 7/2003 | Gelbart | |
| 6,830,558 B2 | 12/2004 | Flaherty et al. | |
| 6,856,399 B2 | 2/2005 | Kuskovsky et al. | |
| 7,074,191 B2 * | 7/2006 | Bosetto et al. | 600/488 |
| 7,121,143 B2 | 10/2006 | Malmstrom et al. | |
| 7,224,470 B2 | 5/2007 | Vaux et al. | |

* cited by examiner

*Primary Examiner* — Laura Bouchelle
(74) *Attorney, Agent, or Firm* — Woodard, Emhardt, Moriarty, McNett & Henry LLP

(57) ABSTRACT

A holographic occlusion detection system has a white-light holographic label placed onto a sensing portion or surface of a pressure sensor connected to infusion tubing. The pressure sensor at the sensing portion can have a relatively thin wall section and may be wider and flatter than a normal cross section of the infusion tubing. The label is then illuminated by a polychromatic light source, and the light reflected off the holographic label is then received by a photodetector. Pressure changes within the tubing cause a change in orientation of the white-light holographic label, thereby resulting in a shift in the peak wavelength of the reflective light sensed by the photodetector. This shift in wavelength can then be calibrated to the swelling of the sensing portion so that pressure within the infusion line can be calculated. In another variation, monochromatic light is reflected off a holographic label, and pressure changes are detected by measuring the amplitude of the reflected light.

36 Claims, 4 Drawing Sheets

HOLOGRAPHIC OCCLUSION DETECTION SYSTEM FOR INFUSION PUMPS

BACKGROUND

Infusion pumps are used in a broad spectrum of medical uses. For example, infusion pumps can be used to deliver nutrients to feed patients as well as medications, such as insulin, chemotherapy drugs, hormones, and opiates, to name just a few. Infusion pumps typically dispense liquids on a continuous, intermittent, and/or a patient controlled basis. One of the main advantages of infusion pumps is their ability to precisely dispense accurate volumes of fluid over long periods of time. To ensure accurate dispensing control, the pressure of the fluid needs to be tightly monitored.

High pressure conditions created by downstream occlusions or blockages in the patient's vein or kinks in the tubing of the infusion pump can be quite dangerous. Likewise, low pressure conditions created by upstream occlusions or lack of fluid can also be problematic. Occlusion detection systems have been developed in which a strain gauge in the pump detects the aggregate force to move the fluid through the entire system. However, the signal-to-noise ratio in these systems is quite poor, and current systems require a very high build up of sensed force in the system before a blockage is detected. These delays in detecting blockages can be very catastrophic.

Occlusion detection systems have been proposed in which the pressure is sensed along the tubing. For example, U.S. Pat. No. 7,121,143 to Malmstrom et al., which is hereby incorporated by reference, describes an optical pressure monitoring system in which a photodetector detects changes in the diameter of the tubing to in turn detect pressure changes by monitoring the amount of light obstructed by the tubing. However, the inventors of the present invention discovered such a system is prone to errors created by the optical properties of the tubing, the tubing's orientation, the liquid being pumped, and/or the ambient conditions. In addition, it was found that tubing with different elastic or other physical characteristics can be accidentally used, which can in turn create erroneous readings.

As another example, U.S. Pat. No. 6,110,153 to Davis et al., which is hereby incorporated by reference, describes an infusion device in which occlusions are detected by internally reflecting light within the tubing. The inventors similarly found this system to be prone to errors created by the properties of the liquid being pumped and by the tubing.

In different fields, other techniques have been proposed to detect pressure. For instance, U.S. Pat. No. 3,590,640 to Cindrich, which is hereby incorporated by reference, detects pressure changes by using optical interferometry to monitor the deflection of a diaphragm. However, it has been discovered that optical interferometry requires precise alignment and matching of the various optical components in order to produce real world accurate measurements, which is not practical in many medical environments.

Thus, there is a need for improvement in this field.

SUMMARY

The holographic occlusion detection system and method described herein addresses the problem of poor occlusion detection within infusion tubing. It solves this problem by placing a white-light holographic label onto a sensing portion or surface of a pressure sensor connected to the infusion tubing. In one example, the pressure sensor at the sensing portion can have a relatively thin wall section and may be wider and flatter than a normal cross section of the infusion tubing. The label is then illuminated by a polychromatic light source, and the light reflected off the hologram is then received by a photodetector. Pressure changes within the tubing result in a physical distortion of the white-light holographic label, thereby resulting in a shift in the peak wavelength of the reflective light sensed by the detector. This shift in wavelength can then be calibrated to the swelling of the sensing portion so that pressure within the infusion line can be calculated. The holographic label can also have a unique optical signature that helps to distinguish the pressure sensor from other types so as to reduce the chance of an improper one being used.

The optical signature can be based on the color of the light reflected off of the holographic label and/or based on the orientation of the holographic label. In another example, the holographic label can be optimized to reflect light based on the color of the light source used. If the wrong diffraction grating was used, it would be easily detected based on the amplitude of light reflected off of the holographic label. For instance, depending on the light source, the holographic label would be optimized for the particular light source. In other examples, the light source, detector, or both can be optimized for the holographic label.

DESCRIPTION OF THE SELECTED EMBODIMENTS

Figure 1:
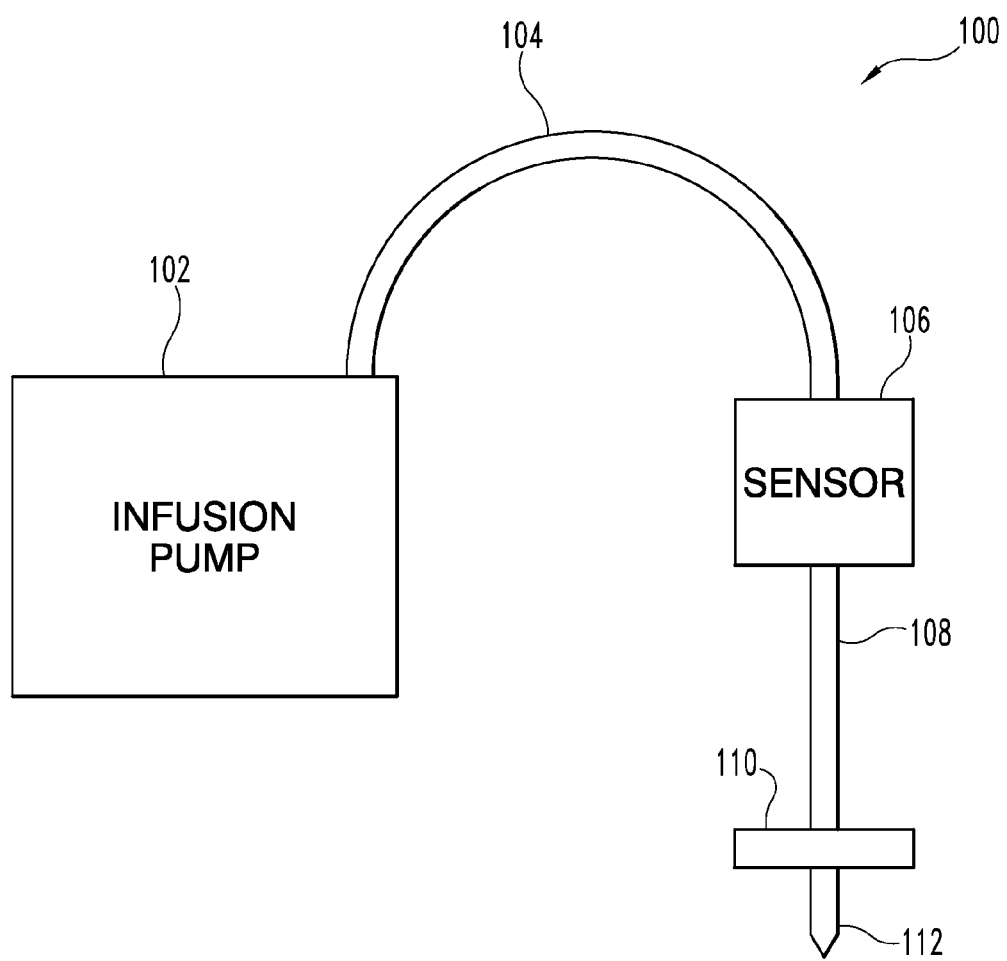
FIG. 1 is a diagrammatic view of an infusion pump system according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiment, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will first appear in FIG. 1, an element identified by a "200" series reference numeral will first appear in FIG. 2, and so on.

FIG. 1 shows a diagrammatic view of an infusion system 100 according to one embodiment. It should be appreciated that this infusion system 100 can be used in a large number of medical applications including, but not limited to, supplying medical-related liquids to patients, such as insulin, saline, nutrients, opiates, and chemotherapy drugs, to name just a few examples. As illustrated, the infusion system 100 includes an infusion pump 102 for pumping a liquid, an upstream section of tubing 104 for transporting the liquid from the infusion pump 102, an occlusion or pressure sensor 106, a downstream section of tubing 108 for transporting the liquid from the pressure sensor 106, and a delivery device 110 for delivering the liquid to the patient. In the illustrated embodiment, the delivery device 110 includes a needle 112 for delivering the liquid to a patient intravenously. The upstream section of the tubing 104 connects the pressure sensor 106 to the infusion pump 102, and the downstream section of tubing 108 in turn connects the delivery device 110 (i.e., the needle 112) to the pressure sensor 106. In other words, the pressure sensor 106 is incorporated into the tubing that supplies the liquid to the patient. In contrast to traditional systems in which a strain gauge in the pump mechanism indirectly infers the pressure, this construction in which the pressure sensor 106 is disposed along the tubing provides faster and more accurate results. As will be explained in greater detail below, the pressure sensor 106 is designed to assist in ensuring that the proper one is used for the particular administered fluid and/or medical procedure. By the very nature of the pressure sensor 106, the infusion system 100 is able to determine if the correct pressure sensor 106 has been installed for the particular situation.

Figure 2:
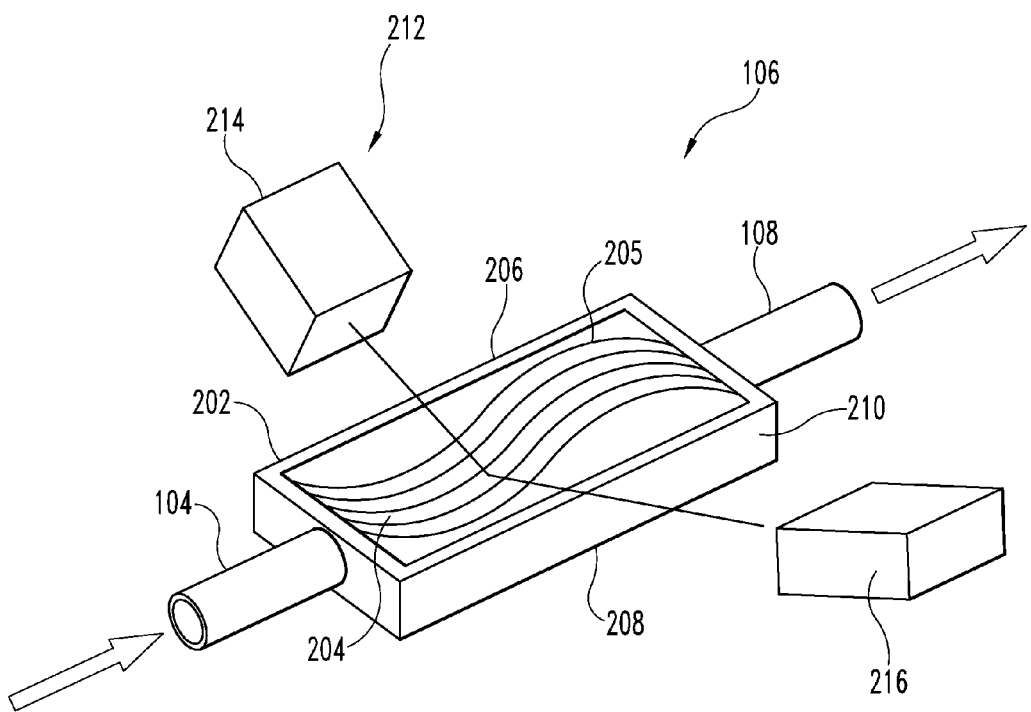
FIG. 2 is a perspective view of a holographic pressure sensor for sensing pressure in the infusion pump system of FIG. 1.

Turning to FIG. 2, it shows a perspective view of one example of the pressure sensor 106. As can be seen, the pressure sensor 106 includes a sensor body 202 and a holographic label 204 with diffraction grating lines 205 affixed to the sensor body 202. The sensor body 202 in the illustrated embodiment is generally rectangular and box shaped. Specifically, the sensor body 202 has a holographic label wall (surface) or sensing portion 206 to which the holographic label 204 is affixed and an opposing surface or wall 208 that is joined to the holographic label wall 206 through sidewalls 210. The sensor body 202 has a hollow interior through which the liquid flows form the upstream section of the tubing 104 to the downstream section of tubing 108. Relative to the walls of the tubing and the sidewalls 210, the holographic label wall 206 is more elastic such that it is able to deform as the pressure increases. In the illustrated embodiment, both the holographic label wall 206 and the opposite wall 208 are made from elastic material that is thinner than the rest of the pressure sensor 106 as well as the tubing in order to facilitate deformation as the pressure changes. The holographic label 204 is made of flexible material that is also able to deform as the holographic label wall 206 deforms. The holographic label 204 in the depicted embodiment is a rainbow transmissive or polychromatic (e.g., white-light) type hologram. With the holographic label 204 being a rainbow transmissive type, less expensive and simpler optics can be used because, among other things, the optics do not require monochromatic light sources, such as expensive lasers.

The pressure sensor 106 is specifically designed to sense pressures based on a number of factors to ensure accurate results, including the physical characteristics of the infusion pump 102, the tubing, the delivery device 110, and the fluid being pumped along with the medical requirements of the patient. In other words, the operational tolerances or sensitivity of the pressure sensor 106 is selected based on the parameters for the specific medical use. The elastic properties and thickness of the holographic label wall 206 along with the holographic label 204 are selected depending on the range of pressure changes that need to be monitored. To enhance sensitivity, the sensor body 202 is wider and flatter than a normal cross section of the infusion tubing.

The infusion system 100 includes an optical detection system 212 for sensing the distortion of the holographic label 204 as the holographic label wall 206 expands and retracts as the pressure changes. The optical detection system 212 is operatively coupled to the infusion pump 102 to communicate the pressure readings to the infusion pump 102. The infusion pump 102 includes one or more processors, memory, and/or other electronics that calculate the pressure based on the readings from the optical detection system 212. The infusion pump 102 outputs the pressure readings to an output device, such as a display and/or a speaker. Looking at FIG. 2, the optical detection system 212 includes a light source 214 and a photosensor or photodetector 216 for detecting light from the light source 214 that is reflected from the holographic label 204. The light source 214 is a broad-spectrum or polychromatic light source, and in one particular example, the light source 214 outputs white-light. The photodetector 216 is configured to detect the wavelength of the light from the light source 214 reflected off the holographic label 204. It should be noted that the orientation of the light source 214 and photodetector 216 relative to the diffraction grating lines 205 of the holographic label 204 are perpendicular or at least transverse with respect to one another. In other words, in each case, the light shines perpendicular relative to the diffraction grating lines 205 on the holographic labels 204. This facilitates more accurate readings. By having the light shine in a perpendicular manner, this particular configuration relies on a linear aspect of the diffraction grating lines 205. That is, the increasing spacing or gapping between the various diffraction grating lines 205 will linearly affect the frequency of light reflected from the diffracting grating, which is then sensed by the photodetector 216. For example, with polychromatic light sources, the wavelength will cause a color shift in the reflected light. This shift is not based on the amplitude of the light but rather the frequency of the light reflected, thereby ensuring more precise measurements. When the pressure changes, the holographic label 204 distorts, which in turn shifts the peak wavelength of light reflected from the holographic label 204 that is sensed by the photodetector 216. This shift in wavelength can then be correlated to the swelling or contraction of the sensor body 202 so that pressure within the infusion line or tubing can be calculated. By measuring the change in the peak wavelength or color, the pressure sensor 106 is less prone to errors due to changes in optical conditions, such as changes in ambient lighting conditions, the intensity of the light output from the light source, etc.

As noted before, traditional interferomic techniques for detecting pressure changes requires expensive, complicated optical components and precise alignment of the components, which is not practical under typical medical conditions. Having the holographic label 204 being a rainbow transmissive type hologram allows the light source 214 to be a broad-spectrum light source, such as a conventional white-light source (e.g., traditional light bulb, halogen light, fluorescent light, LED, etc.) Polychromatic light sources are typically simpler and less expensive than monochromatic light sources, such as lasers, which are usually found in systems that utilize interferomic techniques. With the holographic label 204 being directly attached to the sensor body 202, the need for additional optical components like diffraction gratings is reduced, thereby making replacement easier and less expensive.

In addition, having the holographic label 204 attached to the sensor body 202 reduces the chance for errors. The pressure ranges and sensitivity for the pressure sensor can vary depending on the demands for a particular medical application. The size of the tubing and resulting pressure can also vary depending on the various demands. For instance, one type of pressure sensor 106 may be required for a low pressure or low fluid viscosity use, and a different type might be required for a different medical fluid that is applied with higher pressure. The elastic properties and wall thickness of the holographic label wall 206 can be adjusted depending the required conditions. If the wrong type of pressure sensor 106 is used, dire consequences can occur. To address this issue, the holographic label 204 in one embodiment has a specific optical signature (e.g., light pattern) that the optical detection system 212 uses to identify whether the pressure sensor 106 is the proper one for the particular application. The sequence of the reflected colors, orientation of the diffraction grating lines 205, and/or the optical patterns on the holographic label 204 is used to distinguish one type of pressure sensor 106 from another. The unique optical signature of the holographic label 204 reduces the need for secondary identifiers, such as barcodes, that are not directly related to making measurements. On occasion, such secondary identifiers can be applied to the wrong sensor, and they increase the cost of the sensor. This ability to identify the type of pressure sensor 106 is helpful in medical situations in which the fluid contacting parts are usually disposed of after use. With this design, the relatively inexpensive sensor body 202 and holographic label 204 are disposable after each use, while the relatively more expensive light source 214 and photodetector 216 can be reused. Again, this ability of the holographic label 204 to confirm that the proper infusion tubing kit is installed can be invaluable due to the kit's disposable nature.

Over time, the elastic properties of the sensor body 202 can change and/or degrade, and there can be some variation in properties due to manufacturing differences. With the unique holographic signature of the holographic label 204, the infusion pump 102 is also able to calibrate the pressure sensor 106. Through the unique holographic signature, such as a unique color pattern and/or image pattern, the infusion pump 102 is able to calibrate known pressure levels based on the predefined color and/or image pattern sequences for the holographic label 204 stored in the memory of the infusion pump. For example, the holographic label 204 in one embodiment is designed to progressively reflect red, blue, and green onto the photodetector 216 as the pressure increases from low, to normal, and then to high pressure. Normally, in this example, the photodetector 216 should detect red when low pressure conditions exist, but if blue is detected when no pressure is applied, the infusion pump 102 can recalibrate so as to expect green under normal pressure conditions. Alternatively, the infusion pump 102 can alert the operator when such an out of calibration condition occurs. Moreover, any deviations in the expected sensed light can indicate that the sensor body is improperly installed (i.e., not oriented properly) and/or the pressure sensor 106 is defective, worn, leaking, etc., and the infusion pump 102 can alert the operator to the same. For instance, if the progression of peak colors is not what is expected for a particular pressure sensor 106, the operator can be alerted.

The tubing 104, 108, the pressure sensor 106, and the delivery device 110 in one example are integrated together into a single kit that can be supplied and disposed of as a single unit. Once the kit is properly loaded into the infusion pump and the sensor body 202 is properly loaded/oriented relative to the optical detection system 212, the light source 214 shines light onto the holographic label 204. The photodetector 216 detects the optical signature of the pressure sensor 106 based on the light reflected from the holographic label 204. Based on the detected optical signature, the infusion pump 102 determines whether or not the correct pressure sensor 106 (or kit) has been installed as well as if it has been installed properly. For instance, an improper installation can be detected based on the relative orientation of the diffraction grating lines 205 on the holographic label. For instance, if the holographic label is located at the wrong orientation relative to the photodetector 216, the presence, color, and/or intensity of the light can be different than what is expected, which in turn can indicate an improper installation. If an error has been detected, such as the wrong pressure sensor 106 is installed, the infusion pump 102 takes appropriate actions to correct the error, like alerting the operator about the problem and/or preventing operation of the infusion pump 102. This error detection can also occur during priming of the infusion pump 102. In addition, the infusion pump 102 can initiate a calibration procedure in which known pressures are applied to the pressure sensor 106, and the light reflected off the holographic label is compared to a standard for the particular pressure sensor 106 in the manner as explained above. The readings then are adjusted, or not, depending on the differences between the readings and the standard. After a successful calibration process, the infusion system 100 is ready to pump the fluid.

During operation, the holographic label 204 is illuminated by the polychromatic light source 214, and the light reflected off of the hologram label 204 is then received by the photodetector 216. Pressure changes within the tubing result in a change in stretching or contracting of the holographic label 204, thereby resulting in a shift in the peak wavelength of the reflective light sensed by the photodetector 216. This shift in wavelength can then be calibrated to the swelling of the sensor body 202 so that pressure within the infusion line can be calculated.

Figure 3:
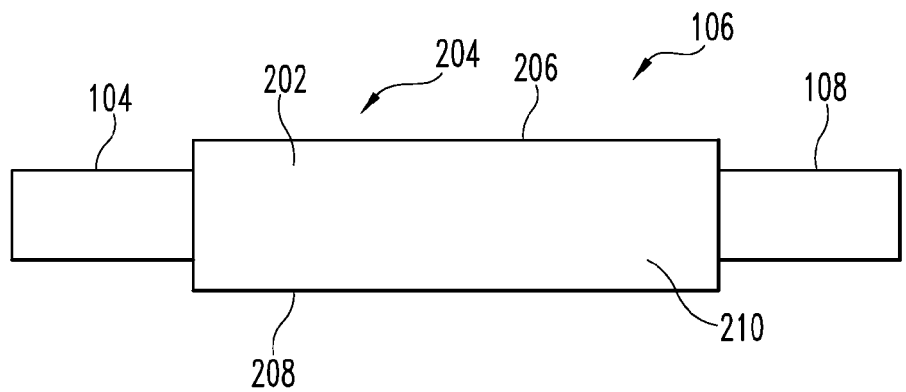
FIG. 3 is a side view of the holographic pressure sensor when a low or no pressure condition exists.
Figure 4:
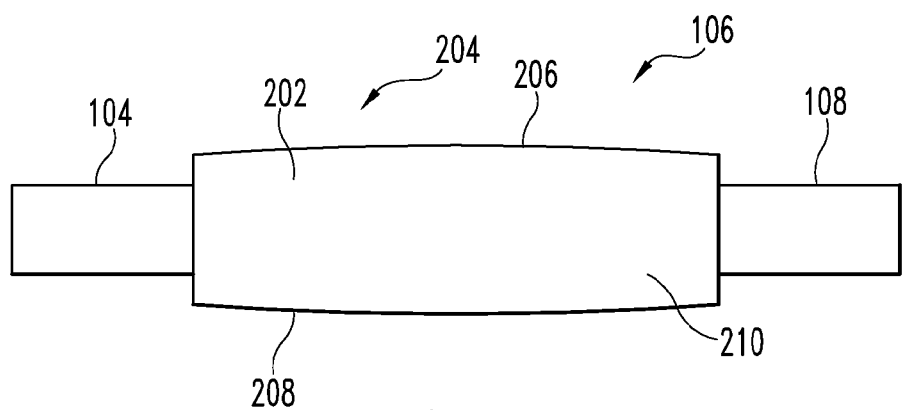
FIG. 4 is a side view of the holographic pressure sensor when normal pressure conditions exist.
Figure 5:
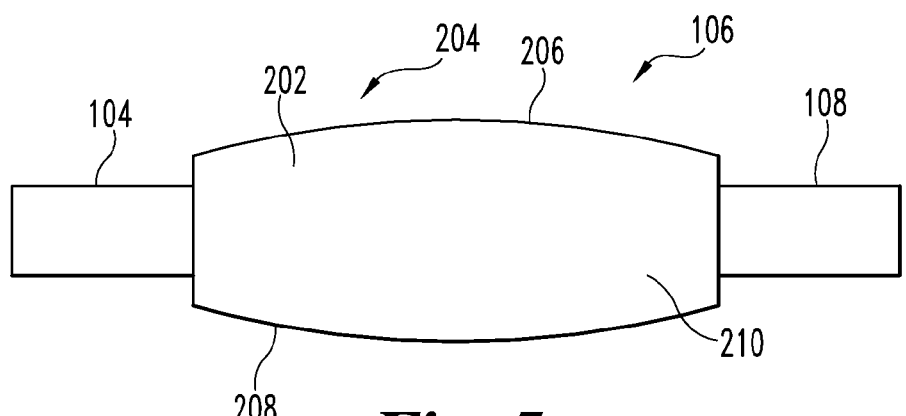
FIG. 5 is a side view of the holographic pressure sensor when a high pressure condition exists.

FIGS. 3, 4, and 5 show a side view of the sensor body 202 at different pressure levels. FIG. 3 shows the state of the sensor body 202 when the fluid has a low pressure. As noted before, the low pressure for example can be the result of kinking or an occlusion in the upstream section of the tubing 104. Looking at FIG. 3, the holographic wall 206 and the holographic label 204 are generally flat. At this position, the color and/or pattern of light received at the photodetector 216 from the holographic label 204 will be indicative of a low pressure. FIG. 4 shows the state of the pressure sensor body 202 under normal pressure conditions. As depicted, the holographic label 204 expands or bulges slightly such that the holographic label 204 reflects the light onto the photodetector with a color and/or pattern that is distinguishable from the other pressure levels. FIG. 5 illustrates the state of the pressure sensor when a high pressure condition occurs. High pressure conditions can occur due to blockages or occlusions within the patient, in the delivery device, and/or along the downstream section of tubing 108. At this high pressure state, the holographic label extends farther such that the color and/or pattern of the light reflected off the holographic label 204 is distinguishable from the other pressure states. Based on the pressure readings from the optical detection system 212, the infusion pump 102 can take any number of actions (or inactions), such as activating an alarm, displaying the pressure readings, and/or regulating the output of the pump, to name just a few examples. Eventually, when appropriate, the pressure sensor 106 or the kit containing the pressure sensor 106 can be removed and discarded, and replaced with a new one.

Figure 6:
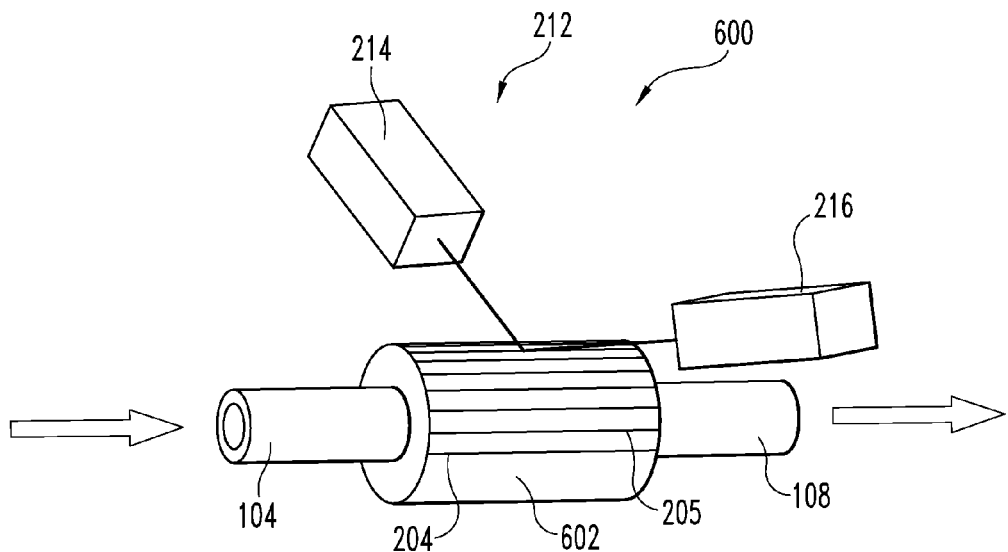
FIG. 6 is a perspective view of a holographic pressure sensor for sensing pressure in which the grating lines run parallel relative to the flow of the fluid.

FIG. 6 illustrates a perspective view of a pressure sensor 600 according to yet another embodiment. As can be seen, the pressure sensor 600 incorporates a number of features common to the previously-described embodiments. For example, the pressure sensor 600 includes the optical detection system 212 with the light source 214 and the photodetector 216 along with the tubing 104, 108. For the sake of clarity as well as brevity, these common components will not be described in detail below, but please refer to the description of the features mentioned in the other parts of the application.

The pressure sensor 600 has a sensor body 602 that has a cylindrical shape. It is contemplated that the cylindrical-shaped sensor body 602 can be used in a wide variety of environments, such as for syringe-type applications. In the illustrated embodiment, the diffraction grating lines 205 extend generally parallel to the flow path of the fluid in the tubing 104, 108. As such, the light source 214 and the photodetector 216 are oriented generally perpendicular to the tubing 104, 108 such that the light from the light source 214 is perpendicular to the diffraction grating lines 205 on the holographic label 204. With this construction, the spacing or gapping between the diffraction grating lines 205 will linearly change as the sensor body 602 shrinks or enlarges which in turn linearly affects the frequency of light reflected from the holographic label 204. This shift is not based on the amplitude but rather on the frequency of the light reflected.

Figure 7:
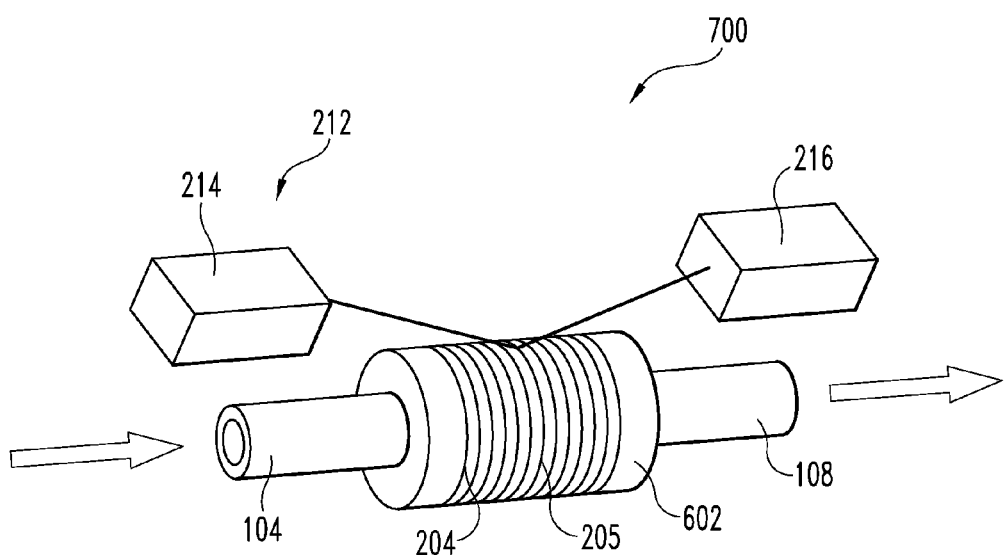
FIG. 7 is a perspective view of a holographic pressure sensor for sensing pressure in a syringe-type setting for an infusion pump in which the grating lines of the holographic label run perpendicular to the flow of the fluid.

FIG. 7 illustrates a perspective view of a pressure sensor 700 according to still yet another embodiment. As can be seen, the pressure sensor 700 in FIG. 7 shows a number of features in common with the one previously described with reference to FIG. 6. For example, the pressure sensor 700 in FIG. 7 includes the optical detection system 212 with the light source 214 and photodetector 216, the tubing 104, 108, and the sensor body 602 having a cylindrical shape. As can be seen, the pressure sensor 700 in FIG. 7 is configured in a fashion similar to the pressure sensor 600 in FIG. 6, but there are a few differences. In particular, the diffraction grating lines 205 of the holographic label 204 generally extend in a circumferential direction relative to the sensor body 602 such that the diffraction grating lines 205 form a series of rings. With the diffraction grating lines 205 extending in a circumferential direction in FIG. 7 rather than the parallel manner relative to the tubing 104 in FIG. 6, the light source 214 and the photodetector 216 the tubing 104, 108 such that the emitted light is perpendicular relative to the grating 205 on the holographic label 204. Again, as the sensor body 602 swells or shrinks, the gapping between the various diffraction grating lines 205 linearly changes which in turn linearly affects the frequency of light reflected from the holographic label 204. This produces relatively easy to interpret linear changes. In the illustrated embodiment, the holographic label 204 extends completely around the sensor body 602, but in other variations, the holographic label can extend only around a portion of the sensor body 602.

Additional Embodiments

While a single embodiment has been described in detail above, there are many variations that can incorporate similar concepts. From the discussion above it should be recognized that the pressure sensor 106 has some unique advantages specially tailored for the medical field. Nevertheless, it is envisioned that various features or concepts related to the pressure sensor 106 can be adapted for use in non-medical fields. Moreover, it also should be understood that infusion system 100 can be used for both human and non-human patients. Although a number of components, such as the infusion pump 102, the tubing 104, 108, the pressure sensor 106, the delivery device 110, the optical detection system 212, etc., have been illustrated as separate components, one or more components and/or combinations thereof can be integrated together. For example, both the light source 214 and the photodetector 216 can be incorporated into the infusion pump 102, and the pressure sensor 106 can be loaded inside the infusion pump 102 when the infusion pump 102 is operating. In the above-described embodiments, the delivery device 110 includes a needle 112 for delivering the liquid intravenously, but it should be recognized that the delivery device 110 can be configured differently to deliver the fluid to the patients in other manners. The delivery device 110 in other embodiments can, for example, include a feeding tube.

The pressure sensor 106 can be positioned at various locations. For instance, the pressure sensor 106 can be located along the tubing at other locations than is shown. While it should be appreciated from the discussion above that there are a number of advantages to the shape of the pressure sensor 106 illustrated in the drawings, it is contemplated that the pressure sensor 106 can be shaped differently in other embodiments. Instead of having the illustrated rectangular, box (flat) shape, the pressure sensor 106 or a portion thereof can have a cylindrical shape, a disc shape, a spherical shape, and/or a cube shape, to name just a few examples. In the illustrated embodiment, the holographic label wall 206 of the sensor body 202 is normally flat when no pressure is applied, but in other embodiments, the holographic label wall 206 (along with other walls) can be normally not flat (e.g., distended) during low pressure conditions. In FIGS. 3, 4, and 5, the holographic label wall 206 and the opposing wall 208 move as the pressure changes, but in other embodiments, the opposing wall 208 can be rigid such that only the holographic label wall 206 moves. In one embodiment, the pressure sensor 106 all or in part is made of an elastic material, such as rubber or plastic, but the pressure sensor 106 can made from other materials.

The optical detection system 212 in other embodiments can further include other optical components, such as lenses, gratings, filters, and/or prisms, to name just a few examples. In the depicted embodiment, the holographic label 204 can be secured to the sensor body 202 through any number of techniques including, but not limited to, via an adhesive, ultrasonic welding, stitching, etc. Moreover, the material forming the holographic label 204 can be directly applied to the holographic label wall 206 through any number of deposition techniques including ink jet printing, screen printing, painting, hot stamping, and/or die coating, to just name a few examples. As described, the holographic label 204 was distinct from the holographic label wall 206, but in other variations, the holographic label 204 is integrally incorporated into the holographic label wall 206. In addition, the holographic label 204 can be located at different locations on the sensor body than is shown. The holographic label 204 in the above-described embodiment has a specific color pattern that changes depending on its distortion relative to its original size and location to the photodetector 216 as the holographic label wall 206 deforms. In further embodiments, the holographic label 204 can include specific image patterns and/or darkened area patterns so as to enhance the unique optical signature, provide additional information, and/or improve measurement precision. The optical signature can be unique for each individual pressure sensor 106 for tracking purposes or unique for each type of pressure sensor 106. For instance, the holographic label 204 in one variation has a unique holographic image. Of course, other color and/or image patterns can be used in other embodiments.

The sensor body 602 in FIGS. 6 and 7 is illustrated as having a larger diameter in comparison to the tubing 104, 108, but it is envisioned that in other variations, the sensor body 602 can be have the same or smaller diameter as compared to the tubing 104, 108. In the embodiment illustrated in FIG. 6, the holographic label 204 is only partially wrapped around the sensor body 602, but it is contemplated that in other embodiments the holographic label 204 can be wrapped completely around the sensor body 602 or contain multiple holographic labels 204 at varying radial locations along the sensor body 602.

The above-described sensors can be used to measure pressure in other manners. For instance, instead of detecting pressure changes through frequency shifts, the pressure changes can be detected at least in part based on the amplitude of the reflected light. Specifically, the light source 214 in another example emits monochromatic light, and the pressure change is measured through the change in intensity of the reflected light as the holographic label 204 expands and contracts.

Definitions

For the purposes of interpreting the specification and claims, the following definitions apply:

The term "fluid" generally means a continuous amorphous substance that tends to flow and to conform to the outline of its container, like a liquid or gas.

The term "holographic label" means a surface that provides or reflects different wavelengths of light at different angles. The holographic label can include, but is not limited to, diffraction gratings and other dispersive optical devices like prisms.

The term "infusion pump" generally means a device that releases a measured amount of a substance in a specific period of time in order to infuse fluids, such as medications or nutrients, into a subject's body. The infusion pump can administer the fluid in a number of manners including, but not limited to, intravenously, subcutaneously, arterially, gastrically, and/or epidurally.

The term "light" is used in the broader sense to mean electromagnetic radiation of any wavelength, including electromagnetic radiation that is visible or invisible to the normal unaided human eye.

The term "light source" means broadly any device or object that generates or otherwise provides light. Nonlimiting examples of light sources include incandescent light bulbs, halogen light bulbs, arc lamps, fluorescent tubes, high intensity lamps, Light Emitting Diodes (LEDs), the sun as well as other stars, chemoluminescence sources, bioluminescence sources, cathode ray tubes, or some combination thereof.

The term "optical signature" means generally a property of light provided by and/or reflected from the holographic label that is able to differentiate one holographic label from another.

The term "polychromatic light" means light composed of more than one wavelength.

The term "photodetector" means a sensor that detects the properties of light including, but not limited to, intensity, frequency, wavelength, phase, color temperature, and/or brightness. The photodetector can sense electromagnetic radiation that is visible or invisible to the normal unaided human eye. Non-limiting examples of photodetectors include spectrometers, spectroscopes, spectrographs, optical detectors, chemical detectors, photoresistors, Light Dependent Resistors (LDRs), photovoltaic cells, photodiodes, photomultiplier tubes, phototubes, phototransistors, Charge-Coupled Devices (CCDs), Complementary Metal-Oxide Semiconductor (CMOS) sensors, reverse-biased Light Emitting Diodes (LEDs) that act as photodiodes, or some combination thereof.

The terms "tube" or "tubing" generally means a conduit including a long hollow object used to hold and/or conduct fluids. Although usually cylindrical in shape, the tubing can have other shapes. Moreover, the tubing can be rigid or flexible, and it can be made from many different materials, like plastic, metals, and glass, to name a few examples.

The language used in the claims and specification is to only have its plain and ordinary meaning, except as explicitly defined above. The words in the above definitions are to only have their plain and ordinary meaning. Such plain and ordinary meaning is inclusive of all consistent dictionary definitions from the most recently published Webster's dictionaries and Random House dictionaries.

It should be noted that the singular forms "a", "an", "the", and the like as used in the description and/or the claims include the plural forms unless expressly discussed otherwise. For example, if the specification and/or claims refer to "a device" or "the device", it includes one or more of such devices.

It should be noted that directional terms, such as "up", "down", "top" "bottom", "upstream", "downstream", etc., are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The publications and patents discussed herein are provided solely for their disclosure prior to the filing date of the present application. Nothing herein is to be construed as an admission that the present invention is not entitled to antedate such publications and patents by virtue of prior invention. Further, the dates of publication provided may be different from the actual publication dates, which may need to be independently confirmed.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A system, comprising:
   a sensor having a sensing portion configured to deform as pressure changes inside the sensor;
   a holographic label affixed to the sensing portion of the sensor, the holographic label being deformable to deform with the sensing portion as the pressure changes inside the sensor;
   a light source configured to shine light onto the holographic label in which the light from the light source is polychromatic light; and
   a photodetector oriented to detect the light reflected from the holographic label.

2. The system of claim 1, in which the sensor has a holographic label wall at the sensing portion that has a wall thickness that differs from the rest of the sensor, the holographic label being attached at the holographic label wall.

3. The system of claim 2, in which the sensing portion is flat.

4. The system of claim 3, further comprising:
tubing configured to transport fluid to the sensor; and
the sensing portion being wider than the tubing.

5. The system of claim 1, in which the holographic label has a unique optical signature that is unique to the sensor.

6. The system of claim 5, in which the unique optical signature includes orientation of diffraction grating lines of the holographic label.

7. The system of claim 1, further comprising:
a delivery device configured to deliver fluid to a patient;
an infusion pump configured to pump fluid to the delivery device, the infusion pump being operatively coupled to the photodetector;
tubing configured to transport the fluid from the infusion pump to the delivery device, the sensor being disposed along the tubing to sense the pressure of the fluid in the tubing; and
the infusion pump being configured to determine the pressure of the fluid in the tubing based on the properties of the light reflected off the holographic label detected with the photodetector.

8. The system of claim 1, in which the holographic label has diffraction grating lines oriented transverse relative to the light source and the photodetector.

9. The system of claim 8, in which the holographic label has diffraction grating lines oriented perpendicular to the light source and the photodetector.

10. The system of claim 1, in which the sensor has a cylindrical shape.

11. The system of claim 10, in which the holographic label wraps completely around the sensor.

12. The system of claim 11, in which the holographic label includes diffraction grating lines that are orientated to create a series of rings around the sensor.

13. The system of claim 10, in which the holographic label includes diffraction grating lines that extend parallel to a fluid flow path in the sensor.

14. The system of claim 1, in which the photodetector is configured to detect color changes of the light reflected from the holographic label as the holographic label deforms, the color changes being indicative of the pressure changes.

15. The system of claim 1, in which the holographic label includes diffraction grating lines being linearly gapped to linearly affect frequency of the light reflected from the holographic label.

16. The system of claim 1, further comprising:
tubing configured to transport fluid to the sensor;
the sensing portion being wider than the tubing;
a delivery device configured to deliver fluid to a patient;
an infusion pump configured to pump fluid to the delivery device, the infusion pump being operatively coupled to the photodetector;
tubing configured to transport the fluid from the infusion pump to the delivery device, the sensor being disposed along the tubing to sense the pressure of the fluid in the tubing;
the infusion pump being configured to determine the pressure of the fluid in the tubing based on the properties of the light reflected off the holographic detected with the photodetector;

the sensor having a holographic label wall at the sensing portion that is thinner than the rest of the sensor, the holographic label being attached at the holographic label wall;
the holographic label having diffraction grating lines oriented transverse to the light source and the photodetector;
the holographic label including diffraction grating lines being linearly gapped to linearly affect frequency of the light reflected from the holographic label;
the photodetector being configured to detect color changes of the light reflected from the holographic label as the holographic label deforms, the color changes being indicative of the pressure changes; and
the holographic label having a unique optical signature that differentiates the sensor from other types of sensors.

17. The system of claim 1, further comprising:
tubing configured to transport fluid to the sensor;
the sensing portion being wider than the tubing;
a delivery device configured to deliver fluid to a patient;
an infusion pump configured to pump fluid to the delivery device, the infusion pump being operatively coupled to the photodetector;
tubing configured to transport the fluid from the infusion pump to the delivery device, the sensor being disposed along the tubing to sense the pressure of the fluid in the tubing;
the infusion pump being configured to determine the pressure of the fluid in the tubing based on the properties of the light reflected off the holographic label detected with the photodetector;
the sensor having a holographic label wall at the sensing portion that is thinner than the rest of the sensor, the holographic label being attached at the holographic label wall;
the holographic label having diffraction grating lines oriented transverse to the light source and the photodetector;
the holographic label including diffraction grating lines being linearly gapped to linearly affect frequency of the light reflected from the holographic label;
the photodetector being configured to detect changes in amplitude of the light reflected from the holographic label as the holographic label deforms, the color changes being indicative of the pressure changes; and
the holographic label having a unique optical signature that differentiates the sensor from other types of sensors.

18. A method, comprising:
shining polychromatic light onto a holographic label, wherein the holographic label includes diffraction grating lines being uniformly spaced to linearly affect frequency of the light reflected from the holographic label;
detecting light reflected off the holographic label disposed on a pressure sensor that deforms as pressure changes inside the pressure sensor; and
determining the pressure inside the pressure sensor based on a property of the light reflected off the holographic label, wherein said determining the pressure inside the pressure sensor includes measuring the frequency of the light reflected from the holographic label.

19. The method of claim 18, in which said determining the pressure comprises detecting changes in peak wavelength of the light reflected off the holographic label.

20. The method of claim 18, further comprising:
wherein the holographic label has an optical signature;
detecting that an incorrect pressure sensor is being used based on the optical signature; and
generating an alert based on said detecting.

21. The method of claim 20, further comprising calibrating pressure readings based on the optical signature.

22. The method of claim 18, in which said determining the pressure comprises detecting changes in amplitude of the light reflected off the holographic label.

23. The method of claim 18, further comprising:
shining monochromatic light onto the holographic label, wherein the holographic label includes diffraction grating lines being uniformly spaced to linearly affect the intensity of the light reflected from the holographic label; and
said determining the pressure inside the pressure sensor includes measuring the intensity of the light reflected from the holographic label.

24. A system, comprising:
a sensor having a sensing portion configured to deform as pressure changes inside the sensor in which the sensor has a cylindrical shape;
a holographic label affixed to the sensing portion of the sensor in which the holographic label wraps completely around the sensor, the holographic label being deformable to deform with the sensing portion as the pressure changes inside the sensor;
a light source configured to shine light onto the holographic label; and
a photodetector oriented to detect the light reflected from the holographic label.

25. The system of claim 24, in which the holographic label includes diffraction grating lines that are orientated to create a series of rings around the sensor.

26. A system, comprising:
a sensor having a sensing portion configured to deform as pressure changes inside the sensor in which the sensor has a cylindrical shape;
a holographic label affixed to the sensing portion of the sensor in which the holographic label includes diffraction grating lines that extend parallel to a fluid flow path in the sensor, the holographic label being deformable to deform with the sensing portion as the pressure changes inside the sensor;
a light source configured to shine light onto the holographic label; and
a photodetector oriented to detect the light reflected from the holographic label.

27. A system, comprising:
a sensor having a sensing portion configured to deform as pressure changes inside the sensor;
a holographic label affixed to the sensing portion of the sensor, the holographic label being deformable to deform with the sensing portion as the pressure changes inside the sensor, wherein the holographic label has a unique optical signature, wherein the unique optical signature includes a sequence of colors reflected from the holographic label;
a light source configured to shine light onto the holographic label; and
a photodetector oriented to detect the light reflected from the holographic label.

28. The system of claim 27, in which the unique optical signature includes orientation of diffraction grating lines of the holographic label.

29. The system of claim 27, further comprising:
an infusion pump operatively coupled to the photodetector, the infusion pump being configured to calibrate to known pressure levels based on the sequence of the colors reflected from the holographic label.

30. The system of claim 27, in which the unique optical signature includes optical patterns on the holographic label.

31. The system of claim 30, further comprising:
an infusion pump operatively coupled to the photodetector, the infusion pump being configured to calibrate to known pressure levels based on a sequence of the optical patterns reflected from the holographic label.

32. The system of claim 27, further comprising:
an infusion pump operatively coupled to the photodetector, the infusion pump being configured to calibrate to known pressure levels based on the unique holographic signature.

33. A system, comprising:
a sensor having a sensing portion configured to deform as pressure changes inside the sensor;
a holographic label affixed to the sensing portion of the sensor, the holographic label being deformable to deform with the sensing portion as the pressure changes inside the sensor, wherein the holographic label has a unique optical signature;
a light source configured to shine light onto the holographic label;
a photodetector oriented to detect the light reflected from the holographic label; and
an infusion pump operatively coupled to the photodetector, the infusion pump being configured to calibrate to known pressure levels based on the unique holographic signature.

34. The system of claim 33, in which the unique optical signature includes orientation of diffraction grating lines of the holographic label.

35. The system of claim 33, in which the unique optical signature includes optical patterns on the holographic label.

36. The system of claim 35, in which the unique optical signature further includes a sequence of colors reflected from the holographic label.

* * * * *